United States Patent [19]

Otsuka et al.

[11] Patent Number: 4,485,087

[45] Date of Patent: Nov. 27, 1984

[54] PROCESS FOR OBTAINING COMPOSITE PHARMACEUTICAL PREPARATION

[75] Inventors: Saburo Otsuka; Yuusuke Ito; Toshiyuki Yoshikawa; Shoichi Tokuda, all of Osaka, Japan

[73] Assignee: Nitto Electric Industrial Co., Ltd., Osaka, Japan

[21] Appl. No.: 357,540

[22] Filed: Mar. 12, 1982

[30] Foreign Application Priority Data

Mar. 13, 1981 [JP] Japan ................................. 56-37016

[51] Int. Cl.³ ..................... A61L 15/03; A61F 13/00; A61K 9/70
[52] U.S. Cl. ...................................... 424/28; 604/896; 427/3
[58] Field of Search .................. 427/3, 2; 424/21, 28; 604/896, 897; 128/156

[56]   References Cited

U.S. PATENT DOCUMENTS 3,121,021 2/1964 Copeland ........................... 128/156
3,731,683 5/1973 Zaffaroni ........................... 126/156
3,769,071 10/1973 Trancik ................................ 424/28
4,060,084 11/1977 Chandrasekaran ................ 604/897
4,201,211 5/1980 Chandrasekaran ................ 604/897
4,286,592 9/1981 Chandrasekaran ................ 128/156

Primary Examiner—Sam Silverberg
Attorney, Agent, or Firm—Sughrue, Mion, Zinn, Macpeak & Seas

[57] ABSTRACT

A process for obtaining a composite pharmaceutical preparation which comprises coating or laminating a composition comprising
(a) an adhesive substance having a pressure-sensitive adhesive property at room temperature, and
(b) a percutaneous absorption type medicine which is solid at 0° C.

onto a polymer film capable of allowing the medicine in contact therewith to migrate through the polymer film, the composition being prepared by adding the medicine to the adhesive substance in a higher concentration than the solubility thereof in the adhesive substance.

18 Claims, No Drawings

PROCESS FOR OBTAINING COMPOSITE PHARMACEUTICAL PREPARATION

FIELD OF THE INVENTION

This invention relates to a process for obtaining a novel composite pharmaceutical preparation which enables increasing the amount of medicine incorporated per unit area of the preparation.

BACKGROUND OF THE INVENTION

There have heretofore been proposed various percutaneous absorption type pharmaceutical preparations which are formed by incorporating a medicine in a polymer substance having a pressure-sensitive adhesive property at room temperature (e.g., about 20°–30° C.) (e.g., an adhesive substance) and providing it on a support.

Recently, it has been attempted to incorporate a medicine in a polymer substance in a higher concentration than the solubility thereof in the polymer substance, so as to better ensure pharmaceutical effects and to increase the amount of medicine per unit area. However, such excess incorporation of an active ingredient can create a serious problem, viz., a reduction in the pressure-sensitive adhesive property of the polymer substance, due to crystallization of the active ingredient on the surface of the polymer substance layer formed on the support.

Therefore, it has alternatively been attempted to increase the thickness of the polymer substance layer, with the concentration of the active ingredient being under the solubility limit for the polymer substance, thus increasing the amount of active ingredient to be fed per unit area. This attempt, however, has the defects that sufficient pharmaceutical effects do not occur due to an insufficient amount of active ingredient per unit volume, or that an increased adhesive property to the skin causes pain upon peeling off of the preparation.

SUMMARY OF THE INVENTION

One object of the present invention is to provide a process for obtaining a novel composite pharmaceutical preparation which enables an increase in the amount of active ingredient to be fed per unit area without increasing the thickness of an adhesive substance layer, while also preventing crystallization of active ingredient on or in the adhesive substance layer.

Another object of the present invention is to provide a process for obtaining a composite pharmaceutical preparation which enables to comparatively freely control release speed of the incorporated active ingredient.

It has now been found that the above-described objects can be attained by coating or laminating a composition prepared by adding a percutaneous absorption type medicine which is solid at 0° C. to an adhesive substance in a higher concentration than the solubility thereof in the adhesive substance, onto a polymer film (including a polymer sheet) capable of allowing a medicine in contact therewith to migrate therethrough.

DETAILED DESCRIPTION OF THE INVENTION

With the thus-formed preparation, excess medicine above the solubility limit is incorporated in the composition layer formed by directly coating the composition on a polymer film or by previously forming on a releasing liner and transferring the previously formed layer onto a polymer film will migrate into the polymer film before crystallization of the medicine. Thus, there can be obtained a composite pharmaceutical preparation which does not undergo crystallization of the medicine, over a period of time, on the composition layer.

The thus-obtained composite pharmaceutical preparation exhibits substantially the same effect as is obtained by increasing the amount of medicine per unit area, because when the preparation is applied to the skin, the medicine in the adhesive substance is gradually absorbed through the skin, and the medicine in the polymer film is supplied to the adhesive substance layer in amounts corresponding to the decrease due to the percutaneous absorption.

Thus, it can be understood that a composite pharmaceutical preparation with rapid effects can be obtained by satisfying the following conditions: solubility of the medicine in the adhesive substance > > solubility of the medicine in the polymer film; and thickness of the adhesive substance layer < thickness of the polymer film. Furthermore, a composite pharmaceutical preparation with delayed effects can be obtained by satisfying the following conditions: solubility of the medicine in the adhesive substance < < solubility of the medicine in the polymer film; and thickness of the adhesive substance < thickness of the polymer film. Still further, a composite pharmaceutical preparation with rapid and long acting effects can be obtained by adjusting the concentration of the medicine in both the adhesive substance layer and the polymer film to saturated solubility levels, provided that solubility of the medicine for the adhesive substance > solubility of the medicine for the film and that thickness of the adhesive substance layer < thickness of the polymer film.

Exemplary materials to be used for forming the composite preparation of the present invention are described below.

(1) A polymer film (or sheet) capable of allowing a medicine in contact therewith to migrate therethrough is a film (preferably having a thickness of from about 10 to 1,000 μm) of a homopolymer or copolymer alone having a glass transition temperature (Tg) of from −50° to 100° C., preferably −40° to 60° C. or of a mixture containing at least 10 wt% of said polymer. For example, there are illustrated polyvinyl acetate, a copolymer of vinyl acetate and a monomer copolymerizable with vinyl acetate, and a polymer containing alkoxy acrylate.

Polymers having a Tg of less than −50° C. are physically too weak, and polymers having a Tg of more than 100° C. have insufficient flexibility and irritate the skin, thus being undesirable.

From the viewpoint of imparting self-supporting properties to the composite pharmaceutical preparation, it is preferable to laminate, on the opposite side of the polymer film, a film which substantially does not allow a medicine to migrate therethrough (medicine-impermeable). As such film, there are illustrated those which are composed of polyethylene, polypropylene, polyvinylidene chloride, polyester, polyamide, cellophane, metal foil, and the like.

(2) The adhesive substance having a pressure-sensitive adhesive property at room temperature is not particularly limited, so long as it ensures that the pharmaceutical preparation will closely adhere to the skin for a predetermined period of time, possesses a suitable compatibility with the medicine, and does not adversely affect releasability of the medicine, with synthetic resins and rubber having a Tg of from −70° to −10° C. being preferable.

Adhesive substances having a Tg of less than −70° C. are not suitable for use in the invention in that they reduce the shape retention properties of the base material and leave residues on the skin, and furthermore, in peeling the pharmaceutical preparation, they provide physical irritation to the skin. Also, adhesive substances having a Tg of more than −10° C. are not suitable for use in the invention since they reduce the mobility of the medicine in the adhesive substance, reduce the releasability thereof, and, furthermore, reduce the adhesive property of the pharmaceutical preparation to the skin.

Polymers having a Tg of −55° to −25° C. are most preferable. The adhesive substances having a Tg of −70° to −10° C. and exhibiting a pressure sensitivity at room temperature can be prepared from a system selected from the group consisting of the synthetic resins and/or rubbers as set forth below:

Synthetic resins include polyvinyl alkyl ethers, polyacrylates, polymethacrylates, polyurethanes, polyesters, polyamides, and ethylene-vinyl acetate copolymers. Rubbers include styrene-isoprene-styrene block copolymer rubber, styrene-butadiene rubber, polybutene rubber, polyisoprene rubber, butyl rubber, silicone rubber, and natural rubber.

When these synthetic resins or rubbers per se do not have a Tg falling within the above-described range, they can be used in combination with other polymers, or alternatively, additives which are generally known can be added to adjust the Tg to fall within the desired range.

It has been found that acryl-based copolymers can meet the above-described requirements of adhesive property, compatibility, solubility, and releasability most surely and by a relatively simple procedure.

Preferred acryl-based copolymers contain at least 50% by weight of alkyl acrylate or alkyl methacrylate containing on the average at least 4 carbon atoms in the alkyl moiety.

These acryl-based copolymers exhibit a good adhesive property to the skin and good solubility to medicines, and furthermore, irritate the skin less and hold the medicine stably.

The acryl-based copolymers as used herein include copolymers of alkyl acrylate or methacrylate and other copolymerizable functional monomers. These monomers are compounded in an amount of from 0% to 20% by weight, and preferably from 0.5 to 15% by weight.

By varying the amount of the monomer added, the cohesive properties of the resulting acryl-based coolymer can be changed, and therefore, the release rate and/or release amount of the medicine from the base material can be controlled. Also, it is possible to increase the hydrophilic properties of the acryl-based copolymer by selecting particular types of monomer.

In addition, the acryl-based copolymers as used herein include copolymers of alkyl acrylate or methacrylate and other copolymerizable vinyl ester monomers. These monomers are compounded in an amount of from 0 to 40% by weight, and preferably from 10 to 30% by weight. Acryl-based copolymers containing such vinyl ester monomers have a high solubility to the medicine.

Thus, it can be understood that acryl-based copolymers composed of at least 50% by weight of alkyl acrylate or methacrylate, from 0 to 20% by weight of functional monomer copolymerizable with the alkyl acrylate or methacrylate, and from 0 to 40% by weight of vinyl ester monomer copolymerizable with the alkyl acrylate or methacrylate are suitable to support therein a percutaneous absorption type medicine which is solid at 0° C.

(3) Percutaneous absorption type medicines which are solid even at 0° C. are set forth below:

(i) Corticosteroids: for example, hydrocortisone, prednisolone, paramethasone, beclomethasone propionate, flumethasone, betamethasone, beclomomethasone propionate, dexamethasone, triamcinolone, triamcinolone acetonide, fluocinolone, fluocinolone acetonide, fluocinolone acetonide acetate, clobetasol propionate, etc.

(ii) Analgesic anti-inflammatory agents: for example, acetaminophen, mefenamic acid, flufenamic acid, indomethacin, diclofenac, alclofenac, oxyphenbutazone, phenylbutazone, ibuprofene, flurbiprofen, salicylic acid, l-menthol, camphor, the composition thereof, etc.

(iii) Hypnotic sedatives: for example, phenobarbital, amobarbital, cyclobarbital, etc.

(iv) Tranquilizers: for example, fluphenazine, thioridazine, diazepam, lorazepam, flunitrazepam, chlorpromazine, etc.

(v) Antihypertensives: for example, clonidine, kallikrein, etc.

(vi) Antihypertensive diuretics: for example, hydrothiazide, bendroflumethiazide, etc.

(vii) Antibiotics: for example, penicillin, oxytetracycline, fradiomycin sulfate, erythromycin, chloramphenicol, etc.

(viii) Anesthetics: for example, lidocaine, benzocaine, ethyl aminobenzoate, etc.

(ix) Antimicrobial agents: for example, benzalkonium chloride, nitrofurazone, nystatin, acetosulfamine, clotrimazole, etc.

(x) Antifungal agents: for example, pentamycin, amphotericin B, pyrrolnitrin, clotrimazole, etc.

(xi) Vitamins: for example, vitamin A, ergocarciferol, chlolecarciferol, octotiamine, riboflavine butyrate, etc.

(xii) Antiepileptics: for example, nitrazepam, meprobamate, etc.

(xiii) Coronary vasodilator: for example, nitroglycerin, dipyridamole, isosorbide dinitrate, erythritol tetranitrate, pentaerythritol tetranitrate, etc.

(xiv) Antihystaminic agents: for example, diphenhydramine hydrochloride, chlorpheniramine, diphenylimidazole, etc.

These medicines may be used, if desired, in combinations of two or more thereof.

(4) As other optional ingredients, fillers and absorption promotors can also be incorporated in order to better achieve the objects of keeping the shape retention properties of the base material, increasing the absorbability of the medicine through the skin into the body, and so forth. In addition, the base material may contain small amounts of additives such as a tackifier and a softening agent.

Fillers which can be used include fine silica powder, titanium white, and calcium carbonate. Absorption promotors which can be used include alcohols such as propylene glycol and diethylene glycol, salicylic acid, urea, allantoin, dimethyl sulfoxide, dimethylacetamide, dimethylformamide, diisopropyl adipate, diethyl sebacate, ethyl laurate, and the like.

The amount of filler added is 20% by weight or less based on the weight of the resulting composition, and the amount of the absorption promotor added is 30% by weight or less based on the weight of the resulting composition.

In the process of the present invention, the amount of a medicine to be incorporated in the composition is adjusted to from about 0.5 to 20% by weight, and preferably from 2 to 15% by weight, based on the total weight of the composition, though varying depending upon the particular kind of medicine, the solubility of the medicine in the adhesive substance and the polymer film, and the thickness of the adhesive substance layer or polymer film.

The composition containing the medicine in a concentration more than the saturated concentration for the adhesive substance is usually provided in a thickness of from 5 to 500 μm, entirely or partly, on the polymer film through which the medicine can migrate (or, with a laminate of said polymer film and a film through which medicines cannot migrate, on the surface of said medicine-migrating polymer film).

As is described above, the composite pharmaceutical preparation obtained by the process of the present invention has the advantages that it does not undergo crystallization of a medicine on the surface of an adhesive layer (base material layer) in spite of incorporation of a medicine in a large amount per unit area, that it closely adheres to the skin to ensure good percutaneous absorption of the medicine with freely controlling the pharmaceutical effects.

The present invention will now be described in more detail by reference to examples of preferred embodiments of the present invention which, however, are not to be construed as limiting the present invention in any way. Additionally, parts are by weight.

EXAMPLE 1

96 g of isooctyl acrylate and 4 g of acrylic acid were placed in a three-necked flask, and 25 g of ethyl acetate containing 0.2 g of azobisisobutyronitrile was added thereto. The atmosphere inside the flask was replaced by an inert gas. Then, the temperature of the contents was raised to 60° C. to start the reaction, and the reaction was continued for 5 hours at 62° to 65° C. during which ethyl acetate was dropwise added thereto, followed by aging for 2 hours at 75° C. to 77° C. to obtain a copolymer solution of 195 poises (30° C.) containing 30 wt% of solids.

1.25 g of prednisolone was added thereto per 100 parts of the solids in the solution, and the resulting mixture was coated and dried on a releasing liner in a dry thickness of 40 μm to obtain a base material film (adhesive substance film).

On the other hand, a 40 μm thick ethyl acrylate-vinyl acetate copolymer film (ethyl acrylate:vinyl acetate=2:1 by weight) through which the medicine can migrate was laminated on one side of a 12.7 μm thick polyester film through which the medicine cannot migrate, to prepare a laminate film.

The above prepared base material film was superposed and press bonded on the copolymer film surface of the laminate film to obtain a composite pharmaceutical preparation.

EXAMPLE 2

10 Parts of isosorbide dinitrate was added to 100 parts of solids in the copolymer solution used in Example 1, and the resulting mixture was coated and dried on a releasing liner in a dry thickness of 40 μm to obtain a base material film (adhesive substance film).

On the other hand, a 100 μm thick laminate film was obtained by co-extruding an ethylene-vinyl acetate copolymer (through which the medicine can migrate) containing 40% by weight of vinyl acetate and polyethylene (through which the medicine cannot migrate) (thickness of the copolymer film: 40 μm).

On the copolymer film surface of this laminate film was superposed and press bonded the above prepared base material film to prepare a composite pharmaceutical preparation.

EXAMPLE 3

A composition composed of 45 parts of polyisoprene rubber, 15 parts of liquid paraffin, 10 parts of lanolin, and 30 parts of aliphatic petroleum resin was melted at 110° to 125° C. for 5 hours in an inert gas and, after cooling to 80° C., 3 parts of indomethacin was added thereto. The resulting mixture was coated on a releasing liner in a thickness of 100 μm to obtain a base material film (adhesive substance film).

On the other hand, a laminate film was obtained by heat pressing a 40 μm thick vinyl acetate-butyl acrylate-methoxyethyl acrylate (40:30:30 by weight) copolymer film (through which the medicine can migrate) and a 50 μm thick polyvinylidene chloride film (through which the medicine cannot migrate) to each other.

On the copolymer film surface of this laminate film was superposed and press bonded the above prepared base material film to obtain a composite pharmaceutical preparation.

Tables 1 and 2 show the results of the tests on the preparations obtained in Examples 1 to 3. Table 1 shows the time by which the medicine crystallized, and Table 2 adhesion to skin, adhesion and retention to a Bakelite plate. Comparative Examples 1 to 3 in Table 1 and Table 2 respectively correspond to Examples 1 to 3. In Comparative Examples 1 to 3, the base material films were respectively press bonded onto a polyester film, polyethylene film, and polyvinylidene chloride film through which the medicine cannot migrate.

TABLE 1

| | Crystallization of Medicine | | | | | |
|---|---|---|---|---|---|---|
| | Storage Days | | | | | |
| | 1 Day | 3 Days | 5 Days | 10 Days | 30 Days | 90 Days |
| Example 1 | none | none | none | none | none | none |
| Comparative Example 1 | none | in part | in part | in part | in part | about half* |
| Example 2 | none | none | none | none | none | none |
| Comparative Example 2 | none | in part | about half* | mostly** | mostly** | mostly** |
| Example 3 | none | none | none | none | none | none |
| Comparative Example 3 | in part | in part | about half* | about half* | about half* | about half* |

Storage conditions: 25° C., 65% R.H.
*About half of the medicine crystallized.
**Most of the medicine crystallized.

TABLE 2

|  | Adhesion to Skin Storage Days | | | Adhesion to Bakelite Plate (g/12 mm) Storage Days | | | Retention to Bakelite Plate (min) Storage Days | | |
| --- | --- | --- | --- | --- | --- | --- | --- | --- | --- |
|  | 1 Day | 10 Days | 90 Days | 1 Day | 10 Days | 90 Days | 1 Day | 10 Days | 90 Days |
| Example 1 | good | good | good | 680 | 670 | 690 | 16 | 14 | 18 |
| Comparative Example 1 | good | good | fair | 650 | 620 | 520 | 17 | 23 | break |
| Example 2 | good | good | good | 650 | 650 | 670 | 23 | 24 | 25 |
| Comparative Example 2 | good | fair | bad | 640 | 320 | 80 | 21 | 38 | break |
| Example 3 | good | good | good | 450 | 430 | 380 | 51 | 40 | 41 |
| Comparative Example 3 | good | fair | bad | 430 | 410 | 300 | 48 | 150 | break |

Methods for measuring adhesion and retention shown in Table 2 are as follows.

ADHESION TO BAKELITE PLATE

A 12 mm wide sample was applied to a bakelite plate and press bonded thereonto by rolling back and forth, one time, a 2.0 kg rubber roller. After storing for 30 minutes, the sample was peeled at one end from the plate to determine the adhesion (peeling angle: 180°; peeling speed: 300 mm/min; 20° C., 65% RH).

RETENTION

One end of a sample (width: 10 mm; length: 100 mm) was applied to an end of a Bakelite plate by 20 mm and, after storing for 20 minutes, a 300 g load was applied to the other end of the sample to measure the time by which it was fallen down from the Bakelite plate (at 40° C.).

Additionally, "break" in Table 2 indicates interlayer break between the base material layer and the film layer or interfacial break from the Bakelite plate.

While the invention has been described in detail and with reference to specific embodiments thereof, it will be apparent to one skilled in the art that various changes and modifications can be made therein without departing from the spirit and scope thereof.

What is claimed is:

1. A process for obtaining a composite pharmaceutical preparation which comprises coating or laminating a composition comprising
   (a) an adhesive substance having a pressure-sensitive adhesive property at room temperature, and
   (b) a percutaneous absorption type medicine which is solid at 0° C.
onto a polymer film capable of allowing the medicine in contact therewith to migrate through the polymer film, the composition being prepared by adding the medicine to the adhesive substance in a higher concentration than the solubility thereof in the adhesive substance, whereupon excess medicine above the solubility limit in the adhesive substance migrates into the polymer film before crystallization of the medicine so that during use medicine in the adhesive substance is gradually adsorbed through the skin and the medicine and the polymer film is supplied to the adhesive substance in an amount corresponding to the decrease due to the adsorption of the medicine through the skin.

2. A process as in claim 1, wherein the polymer film has a glass transition temperature (Tg) of from −50° to 100° C.

3. A process as in claim 2, wherein the polymer film has a glass transition temperature (Tg) of from +40° to 60° C.

4. A process as in claim 1, wherein the opposite side of the polymer film is laminated to a medicine-impermeable film.

5. A process as in claim 4, wherein the medicine-impermeable film is selected from the group consisting of polyethylene, polypropylene, polyvinylidene chloride, polyester, polyamide, cellophane, and metal foil.

6. A process as in claim 1, wherein the adhesive substance is a synthetic resin, rubber, or combination thereof, having a Tg of from −70° to −10° C.

7. A process as in claim 6, wherein the adhesive substance is a synthetic resin, rubber, or combination thereof, having a Tg of from −55° to −25° C.

8. A process as in claim 6, wherein the synthetic resin is selected from polyvinyl alkyl ethers, polyacrylates, polymethacrylates, polyurethanes, polyesters, polyamides, and ethylene-vinyl acetate copolymers, and the rubber is selected from styrene-isoprene-styrene block copolymer rubber, styrene-butadiene rubber, polybutene rubber, polyisoprene rubber, butyl rubber, silicone rubber, and natural rubber.

9. A process as in claim 1, wherein the medicine is incorporated in the adhesive substance in an amount of from about 0.5 to 20% by weight, based on the total weight of the composition.

10. A process as in claim 9, wherein the medicine is incorporated in the high polymer substance in an amount of from about 2 to 15% by weight, based on the total weight of the composition.

11. A process as in claim 1, wherein the thickness of the layer of the composition is from 5 to 500 μm.

12. A process as in claim 1, wherein the polymer film has a glass transition temperature (Tg) of from −50° to 100° C. and the adhesive substance is a synthetic resin, rubber or combination thereof, having a Tg up from −70° to −10° C.

13. A process as in claim 12, wherein the medicine is incorporated in the adhesive substance in an amount of from about 0.5 to 20% by weight, based on the total weight of the composition.

14. A process as in claim 13, wherein the synthetic resin is selected from polyvinyl alkyl ethers, polyacrylates, polymethacrylates, polyurethanes, polyesters, polyamides, and ethylene-vinyl acetate copolymers, and the rubber is selected from styrene-isoprene-styrene block copolymer rubber, styrene-butadiene rubber, polybutene rubber, polyisoprene rubber, butyl rubber, silicone rubber, and natural rubber.

15. A process as in claim 14, wherein the thickness of the layer of the composition is from 5 to 500 μm and wherein the thickness of the polymer film is from about 10 to 1000 μm.

16. A process as in claim 15, wherein the polymer film is selected from polyvinyl acetate, a copolymer of vinyl acetate and a monomer copolymerizable with vinyl acetate, and a polymer containing alkoxy acrylate.

17. A process as in claim 1, wherein the solubility of the medicine in the adhesive substance is much greater than the solubility thereof than in the polymer film and the thickness of the adhesive substance layer is less than the thickness of the polymer film.

18. A process as in claim 1, wherein the solubility of the medicine in the adhesive substance is less than the solubility of the medicine in the polymer film and the thickness of the adhesive substance is less than the thickness of the polymer film.

* * * * *